United States Patent [19]

Guon

[11] 4,244,693

[45] Jan. 13, 1981

[54] METHOD AND COMPOSITION FOR TESTING FOR THE PRESENCE OF AN ALKALI METAL

[75] Inventor: Jerold Guon, Canoga Park, Calif.

[73] Assignee: The United States of America as represented by the United States Department of Energy, Washington, D.C.

[21] Appl. No.: 772,627

[22] Filed: Feb. 28, 1977

[51] Int. Cl.² ...................... G01N 31/22; G01N 33/20
[52] U.S. Cl. .................................. 23/230 L; 252/408; 23/230 R
[58] Field of Search .......................... 23/230 L, 230 R; 252/408 R

[56] References Cited

U.S. PATENT DOCUMENTS

| | | | |
|---|---|---|---|
| 2,228,737 | 1/1941 | Tandberg et al. | 23/230 L |
| 2,708,896 | 5/1955 | Smith et al. | 23/230 R |
| 2,918,033 | 12/1959 | Snyder | 23/230 L X |
| 3,969,077 | 7/1976 | Hill | 23/230 L |

*Primary Examiner*—Robert M. Reese
*Attorney, Agent, or Firm*—James E. Denny; Richard G. Besha; Henry Kolin

[57] ABSTRACT

A method and composition for detecting the presence of an alkali metal on the surface of a body such as a metal plate, tank, pipe or the like is provided. The method comprises contacting the surface with a thin film of a liquid composition comprising a light-colored pigment, an acid-base indicator, and a nonionic wetting agent dispersed in a liquid carrier comprising a minor amount of water and a major amount of an organic solvent selected from the group consisting of the lower aliphatic alcohols, ketones and ethers. Any alkali metal present on the surface in elemental form or as an alkali metal hydroxide or alkali metal carbonate will react with the acid-base indicator to produce a contrasting color change in the thin film, which is readily discernible by visual observation or automatic techniques.

9 Claims, No Drawings

METHOD AND COMPOSITION FOR TESTING FOR THE PRESENCE OF AN ALKALI METAL

BACKGROUND OF THE INVENTION

1. Field of the Invention

The present invention relates to the preparation of a new composition of matter and its use in chemical and other fields. It particularly relates to a composition of matter useful for the detection of the presence of alkali metals, alkali metal hydroxides or alkali metal carbonates on surfaces.

2. Prior Art

Numerous chemical compositions and methods have been suggested heretofore for detecting leaks in vessels. U.S. Pat. No. 3,597,263 suggests a water leak detector, which may be provided in the form of a paint or adhesive tape for application to a metal surface. The indicators suggested comprise (a) a carrier and a strontium chromate/silver sulphate couple as the active indicator, or (b) a carrier and a potassium ferrocyanide/ferric sulphate-inert brightener couple as the active indicator, or (c) a carrier and a potassium ferrocyanide/cupric sulphate-inert brightener couple as the active indicator.

U.S. Pat. No. 3,287,156 suggests a leak-indicating coating for missiles and rockets. The suggested leak-indicating coating comprises an undercoating on the exterior side of the vessel and an overcoating on the undercoating. Each coating comprises a light-colored solid organic material selected from the group consisting of cellulose-base lacquers and solvent-type resins. The undercoating contains phenosafranine dispersed therein, and the overcoating contains a dispersion of phenolphthalein.

Other patents relating to the use of coatings for the detection of leaks are U.S. Pat. Nos. 1,478,445; 1,915,965; 2,228,737; 2,601,840; and 2,708,896.

U.S. Pat. No. 3,814,695 discloses a water washable penetrant composition for the detection of surface defects. The penetrant comprises a vehicle consisting of a vinyl-chloride, vinyl-acetate copolymer resin binder, a solvent and an alkylene oxide condensate non-ionic surfactant containing from about 1–2% by volume of a dye which is soluble in the vehicle.

U.S. Pat. No. 3,652,225 relates to a color method for detecting cracks in metal bodies. A color-forming aqueous acid indicating solution containing halide ions and a color-forming indicator is applied to the surface of a body to be tested. The solution is formulated so that it does not corrode to any significant extent the open surface portion of the body, but is sufficiently reactive to corrode the surface portion within cracks, resulting in the formation of metallic ions. The color-forming indicator is of the type which reacts with the thus-formed metal ions to form a distinctive colored compound at the crack location.

The foregoing methods and compositions, while useful in their respective fields, do not fulfill the need for a composition and method useful for the detection of alkali metals, alkali metal hydroxides or alkali metal carbonates on a metal surface. More particularly, it has been found that a residue of an alkali metal such as sodium on a metal surface will react with water and carbon dioxide in the air to form sodium hydroxide and carbonate, respectively. Even small amounts of any one of these materials on the surface of a metal part for an extended period of time can cause localized surface corrosion, which could result in a failure of the part when it is placed in service. In a nuclear reactor which utilizes a liquid alkali metal such as sodium, potassium or mixtures thereof as a heat exchange fluid, a significant number of parts are exposed to the alkali metal and frequently may have to be removed for cleaning, maintenance or the like. Obviously, there is a need for a method of ensuring that all of the alkali metal has been removed from the surfaces of the part prior to its being exposed to the atmosphere for any extended period of time or being returned to service in the liquid metal environment.

SUMMARY OF THE INVENTION

In accordance with the present invention, there is provided a method for detecting the presence of an alkali metal on the surface of a body such as a metal plate, tank, pipe, or the like. Broadly, the method comprises contacting the surface with a thin film of a liquid composition containing an indicator which will react with the alkali metal, alkali metal hydroxide or alkali metal carbonate to produce a color change in the film which is readily discernible by visual observation, colorimetrically or the like. The liquid composition comprises a light-colored pigment, an acid-base indicator, and a nonionic wetting agent dispersed in a liquid carrier, which comprises a minor amount of water and a major amount of an organic solvent selected from the group consisting of lower aliphatic alcohols, ketones and ethers. The liquid composition also may contain buffers to reduce the sensitivity to the alkali metal when desired as well as thickeners and thixotropic agents to provide desired viscosity and flow properties, depending upon the particular application method desired.

A particularly preferred composition comprises about one part of a light-colored pigment, about one part liquid carrier (having an organic solvent-to-water ratio of about 5:1), about 0.01 part of an acid-base indicator, and about 0.01 parts of a wetting agent.

DETAILED DESCRIPTION OF THE INVENTION

In accordance with the present invention for detecting the presence of an alkali metal on a surface, the alkali metal generally is present as free metal, a carbonate or hydroxide. Specifically, when the alkali metal initially is present on the surface in its elemental form, even in trace amounts, it will readily react with water (either vapor or liquid) or $CO_2$ in the ambient atmosphere to form at least a superficial film of alkali metal hydroxide or carbonate, respectively. To determine the presence of any alkali metal hydroxide or carbonate on a surface, a thin film of a liquid formulation containing an acid-base indicator is applied to the surface, whereby any alkali metal, alkali metal hydroxide or alkali metal carbonate will cause a contrasting color change in the film.

Suitable acid-base indicators include any that effect a color change at a pH of between about 4 and 11 and include, but are not restricted to, phenolphthalein, thymolphthalein, brilliant yellow, thymol blue, cresol purple, neutral red, phenol red, bromthymol blue, chlorphenol red, methyl red, bromcresol green, and alizarine yellow. The particularly preferred acid-base indicators are those which effect a color change within a pH range of between about 7.0 and 9.0, illustrative of which is a preferred indicator, phenol red. Generally, the liquid formulation will contain from about 0.001 to about 0.1 part of an acid-base indicator, and preferably will contain from about 0.005 to about 0.02 part of the selected acid-base indicator.

The acid-base indicator is dispersed in 0.5 to 5 parts and preferably about 1 part of a liquid carrier, which comprises a mixture of water and an organic solvent. Generally, the ratio of organic solvent to water will be within the range of from about 2:1 to 10:1, with a ratio of organic solvent-to-water of about 5:1 being particularly preferred. The particular organic solvent selected is not critical, provided that it has a relatively high volatility and is miscible in water. The preferred organic solvents are the lower aliphatic alcohols, ketones and ethers, including the alcohols and ketones containing from 1 to 3 carbon atoms, and ethers containing from 1 to 5 carbon atoms. Obviously, the organic solvent may be either a single compound or a mixture of one or more of the aforesaid solvents.

To ensure the penetration of the liquid carrier into any crevices or corners of the surface and to enhance the uniform application of a thin film of the formulation to the surface, there also is provided from about 0.005 to about 0.02 part of a wetting agent. A particularly preferred formulation includes about 0.01 part of the wetting agent. Typical wetting agents include the commercially available nonionic surfactants such as the Triton series of surfactants sold by Union Carbide Chemical Company, for example, Triton X-15, Triton X-35, Triton X-45, Triton X-100, Triton X-155, Triton X-405, Triton DN-65 and others in the same series.

Also, certain wetting agent commercially known as Aerosols and made by the American Cyanamid Company have been found suitable for use in the liquid formulation disclosed herein. The foregoing aerosol products generally comprise odorless esters of sulphonated dicarboxylic acid which in its 10% pure state resembles paraffin. For commercial use the mentioned products usually are diluted with water in an amount indicated in the product named by a percentage; thus, Aerosol 75% is an aqueous solution of 75% ester of the mentioned type and 25% deionized water by volume. In general, the mentioned esters are dioctyl sodium sulfosuccinates having the composition $CH_2COO$, $CHCPPC_8H_{17}$, $CO_3NA$, and are soluble in practically all non-aqueous media as well as in water. The foregoing wetting agents and their preparation are known in the art and are suggested by U.S. Pat. Nos. 2,028,091 and 2,176,423, among others.

Other suitable wetting agents for use in the practice of the present invention are commercially available products known as Tergitol Nonionic NPX and Tergitol Nonionic TMN, both of which are sold by Union Carbide Chemical Company. Tergitol Nonionic NPX is a nonyl phenyl polyethylene glycol ether containing 10.5 mols of ethylene oxide, and Tergitol Nonionic TMN is a triethyl nonyl ether of a polyethylene glycol containing 6 mols of ethylene oxide. Numerous other nonionic surfactants also are suitable for use in accordance with the present invention.

In addition, the formulation also should include a light-colored pigment to provide a uniform color to the surface being tested. Generally, the pigment will be provided in an amount of from about 0.5 to 1.5 parts of pigment per part liquid carrier. The particular pigment selected is not critical, provided that it is one which will impart or provide a contrasting color to the selected acid-base indicator and is one which is readily dispersible in the liquid carrier. Various such pigments are well known to those versed in the art. A particularly preferred pigment material, based on its low cost and availability, is Talc, which also is sometimes referred to as soaptone or steatite, and represented by the general formula $3MgO.4SiO_2.H_2O$. Other suitable pigment materials include the various clays such as the kaolin group (alumina-silica-water), the bauxite group (alumina-water), or the like. In addition, purified pigment materials such as alumina ($Al_2O_3$), calcia (CaO), magnesia (MgO) also are suitable.

The method and composition of the present invention are highly sensitive to even trace amounts of an alkali metal present as either a hydroxide or carbonate. In some instances it may be desirable to lower the sensitivity of the invention to the presence of such compounds. This is readily accomplished by the addition of a buffer. The selection of an appropriate buffer is, of course, dependent upon the particular acid-base indicator utilized and well within the skill of those versed in the art. Typically, the buffer will comprise an alkali metal salt of a weak acid such as sodium or potassium citrate. Also, depending upon the method utilized to apply the composition of the present invention to the surface (such as by brush, spray or immersion), it may be desirable to include a thickening and/or thixotropic agent to impart a desired viscosity to the composition. Any of the agents commonly used in water base paints to alter their viscosity characteristics are suitable for use in accordance with the present invention, an exemplary thickening agent being methyl cellulose.

The following example is set forth to further illustrate the advantage and utility of the present invention. All parts and percentages referred to herein are by weight unless otherwise noted.

EXAMPLE

A particularly preferred composition of the present invention was prepared which comprised 1 part talc, 1 part liquid carrier (5 parts methyl alcohol to 1 part water), 0.01 part phenol red, and 0.01 part Triton X-405.

Several test metal coupons were obtained, and some of them were sprayed with dilute solutions of either sodium carbonate or sodium hydroxide and allowed to dry. Thereafter, a thin film of the aforesaid liquid composition was applied to each of the coupons. Those coupons sprayed with either the sodium hydroxide or carbonate displayed a bright red color, whereas the unsprayed coupons had only a white film resulting from the liquid composition. Thus, this example, clearly demonstrates the utility of the present invention to detect trace amounts of sodium present as either a carbonate or hydroxide.

Another advantage of the present invention is that the liquid composition is readily removable by washing with water.

While the particular details set forth above are capable of attaining the objects and providing the advantages herein stated, the specific materials described and the method disclosed are merely illustrative and could be varied through the use of other indicators, organic solvents, pigments, and the like, or different application techniques to produce the same results without departing from the scope of the inventive concept as defined in the appended claims.

What is claimed is:

1. A liquid composition for detecting the presence of an alkali metal on the surface of a body comprising:

a light-colored pigment, an acid-base indicator, and a nonionic wetting agent dispersed in a liquid carrier which comprises a minor amount of water and a major amount of an organic solvent selected from the group consisting of lower aliphatic alcohols, ketones and ethers.

2. The composition of claim 1 wherein said acid-base indicator is one which undergoes a color change at a pH of between about 4 and 11.

3. The liquid composition of claim 1 wherein said organic solvent is selected from the group consisting of alcohols and ketones containing from 1 to 3 carbon atoms and ethers containing from 1 to 5 carbon atoms, and said organic solvent is present in said liquid carrier in an amount to provide a solvent-to-water ratio within the range from about 2:1 to 10:1.

4. The liquid composition of claim 1 wherein said light-colored pigment is talc.

5. A method for detecting the presence of an alkali metal on the surface of a body comprising:
applying to said surface a thin film of a liquid composition comprising a light-colored pigment, an acid-base indicator and a nonionic wetting agent dispersed in a liquid carrier which comprises a minor amount of water and a major amount of an organic solvent selected from the group consisting of lower aliphatic alcohols, ketones and ethers, whereby any alkali metal present on the surface will react with the acid-base indicator to produce a contrasting color change in the thin film which is readily discernable.

6. The method of claim 5 wherein said organic solvent is selected from the group consisting of alcohols and ketones containing from 1 to 3 carbon atoms and ethers containing from 1 to 5 carbon atoms, and said organic solvent is present in said liquid carrier in an amount to provide a solvent-to-water ratio within the range of from about 2:1 to 10:1.

7. The method of claim 5 wherein said light-colored pigment is talc.

8. The method of claim 5 wherein said acid-base indicator is one which undergoes a color change at a pH of between about 7 and 9.

9. The method of claim 8 wherein said acid-base indicator is phenol red.

* * * * *